(12) United States Patent
Ohmura et al.

(10) Patent No.: US 6,312,950 B1
(45) Date of Patent: Nov. 6, 2001

(54) APPARATUS AND METHOD FOR ISOLATING AND RECOVERING CELLS

(75) Inventors: Yoshitaka Ohmura, Hadano; Miyuki Shimizu, Ashigarakami-gun; Tadashi Sameshima, Hadano, all of (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/395,740

(22) Filed: Sep. 14, 1999

(30) Foreign Application Priority Data

Sep. 14, 1998 (JP) .................................................. 10-279364

(51) Int. Cl.[7] .............................. C12N 5/00; C12N 5/02; C12M 1/00; C12M 1/12; A01N 1/02
(52) U.S. Cl. ................... 435/325; 435/283.1; 435/297.1; 435/2; 100/37; 210/483; 210/489; 210/500.1; 422/82.09
(58) Field of Search ........................... 435/325, 2, 283.1, 435/297.1; 210/483, 489, 500.1; 422/82.09; 100/37

(56) References Cited

FOREIGN PATENT DOCUMENTS

| | | |
|---|---|---|
| 0 331 174 | 9/1989 | (EP) . |
| 0 806 475 | 11/1997 | (EP) . |
| 0 928 617 | 7/1999 | (EP) . |

*Primary Examiner*—Christopher R. Tate
*Assistant Examiner*—Randall Winston
(74) *Attorney, Agent, or Firm*—Burns, Doane, Swecker & Mathis, LLP

(57) ABSTRACT

There is proposed an apparatus for isolating and recovering an objective cell, which comprises, a filtering device having a filtering member which is capable of setting a porosity thereof to two or more different porosity, a first line for feeding a priming liquid to the filtering device, a second line for feeding a liquid to be treated containing the cell aimed to isolate to the filtering device, and a third line provided with a storage container for storing the priming liquid that has been passed through the filtering device, wherein the priming liquid stored in the storage container is employed for washing the filtering device. There is also proposed a method for isolating and recovering an objective cell using the aforementioned apparatus.

5 Claims, 2 Drawing Sheets

APPARATUS AND METHOD FOR ISOLATING AND RECOVERING CELLS

BACKGROUND OF THE INVENTION

This invention relates to an apparatus and method for isolating and recovering an objective cell intended to obtain from a liquid to be treated.

When a cell is treated in vitro as in the case of a cell-using therapy, for example, hematopoietic stem cell transplantation, adoptive immunotherapy, gene therapy, etc., or in the case of the culture and preservation of a cell, the isolation of an objective cell intended to be recovered (hereinafter referred to as an objective cell) such as lymphocyte from other components and subsequent concentration of the objective cell have been usually performed.

In the culture of a cell or in the cell-using therapy, it has been a very important subject matter to remove cells other than an objective cell, and further, to remove unwanted liquid components as well as the wastes and metabolic products of cells. In the employment of a preserved cell, it has been also a very important subject matter to remove materials harmful to cells or living body. An example of such harmful material is a cryoprotective agent which is employed for cryopreservation. In view of these problems, there have been proposed various methods of cell-isolation and recovery methods corresponding to these cell-isolation.

The method for isolating cell can be roughly classified into (1) a method based on differences in specific density of cells, such as a sedimentation method, a centrifugation method and a density gradient centrifugation method; (2) an electric separation method based on the surface electric charge of cells; (3) an affinity separation method taking advantage of the antibody specific to the surface antigen of the cells; and (4) a filtering separation method based on the differences in size and in deformability of cells.

These methods (1) to (4), however, are accompanied with the following defects.

In the case of the sedimentation method (1) which is based on the differences in the density of cells, since the objective cell is to be separated by gravity, it takes a long period of time for the isolation of the objective cell, and the isolation efficiency is very poor. Additionally, there are problems that the purity and yield of the objective cell are also low.

With a view to improve the isolation efficiency by using centrifugal force, there has been developed the centrifugation method, which is generally employed as a method for treating a large quantity of cells. However, since this centrifugation method requires a large-scaled and expensive apparatus for an aseptic treatment and recovery of cells, and since differences in density among cells are not so large, the types of cells that can be separated are inevitably restricted.

When it is desired to improve the separability, use is made of the density gradient centrifugation method where a specific density medium whose specific density is strictly adjusted. However, this method is accompanied with problems that it cannot simultaneously treat a large quantity of cells and involves a very complicated operation. Specifically, the objective cell is required to be carefully recovered from an interface formed by density-differences; the operation of removing unwanted cell components is required to be performed in a separate condition from that of removing unwanted liquid components; and the sterility in the recovery operation cannot be ensured unless a clean bench is employed.

Further, in the aforementioned method (1), depending on the condition of the centrifugation, the objective cell may be badly damaged.

In the case of electric separation method (2), since the differences in surface electric charge among the cells are not so large, the separability of the cells is inevitably restricted. Further, the method is not suited for promptly treating a large quantity of cells. Additionally, there is a probability in this method that the objective cell may be badly damaged due to the application of an electric field to the objective cell.

The affinity separation method (3) is most excellent in view of specificity among the aforementioned various isolation methods. However, if the isolated cell is to be recovered using this method, an enzymatic treatment for cleavage an antibody molecule combined to the cell is required. Therefore, it will be confronted with technical problems such as the generation of damage to the objective cell due to the enzymatic treatment, a troublesome operation and the maintenance of the activity of antibody. Additionally, since it employs an expensive antibody, the cost for the isolation of cell will be increased, thus making the method inappropriate for a prompt treatment of a large amount of cells.

The filtering separation method (4) is featured in that it comprises the steps of passing a suspension liquid containing an objective cell through a filtering member so as to capture the objective cell on the filtering member, passing recovering liquid through the filtering member in the direction opposite to that of the capturing step so as to remove the objective cell captured on the filtering member, and recovering the objective cell. Although this filtering separation method is suited for promptly separating a large quantity of objective cell from the unwanted cells as well as from unwanted liquid components, this method is defective in that the recovery ratio of the objective cell is low. This defect can be ascribed to the fact that the fine pore diameter of the filtering member is constant throughout a sequence of the treatment procedures.

Specifically, when the pore size of the filtering member is set relatively larger with a view to improve the releasability of the objective cell at the step of recovering, the amount of the objective cell that passes through the filtering member without being captured by the filtering member will be increased. On the contrary, if the pore size of the filtering member is set relatively smaller, the amount of the objective cell that passes through the filtering member will be minimized, thereby increasing the quantity of objective cell that can be captured by the filtering member. However, the adhesivity of the objective cell to the fine pore of the filtering member will be increased so that the releasability of the objective cell at the step of recovering the objective cell will be deteriorated, thus making it impossible to recover the objective cell at a high yield. In addition, the removability of unwanted cells will be also deteriorated.

Under the circumstances, depending on the type of the objective cell, a filtering member having a suitable pore size which is capable of satisfying not only the capturability but also the releasability of the objective cell is required to be selected.

Incidentally, it is possible in this filtering separation method to decrease more or less the quantity of the objective cell that passes through the filtering member and to increase the capturing ratio of the objective cell by reducing the quantity of feeding the suspension of cells on the occasion of the filtration. However, if the feeding quantity of the suspension of cells is reduced, the throughput per unit time of the suspension of cells is also caused to decrease, thus spoiling the advantage of the filtering separation method, i.e. a prompt treatment of large quantity of the suspension of cells.

It is also possible in this filtering separation method to improve the releasability of the objective cell that has been captured on the filtering member by increasing the feeding quantity of the recovery liquid on the occasion of the recovery of the objective cell. However, if the feeding quantity of the recovery liquid is increased, the objective cell may be increasingly damaged, thus deteriorating the characteristics and quality of the recovered objective cell.

As described above, the prior arts have the merits and demerits in the means for isolating the objective cell from the unwanted components as well as in the means for recovering the isolated cell. Under the circumstances, the aforementioned methods have been suitably selected or suitably combined depending on the purpose and the required level of isolation.

BRIEF SUMMARY OF THE INVENTION

This invention has been made to overcome the aforementioned defects of the prior arts, in particular, the aforementioned defects accompanied with the conventional filtering separation method. Therefore, the objects of the present invention are to provide an apparatus and method for easily and aseptically treating a suspension of cells so as to isolate and recover an objective cell, without deteriorating the quality and characteristics of the objective cell.

These objects of the present invention can be realized by the following features (1) to (25).

(1) An apparatus for isolating and recovering an objective cell, which comprises;
a filtering device having a filtering member which can be set to two or more different porosity;
a first line for feeding a priming liquid to the filtering device;
a second line for feeding a liquid to be treated containing the objective cell to the filtering device; and
a third line provided with a storage container for storing the priming liquid that has been passed through the filtering device;
the priming liquid stored in the storage container being employed for washing the filtering device.

(2) The apparatus for isolating and recovering an objective cell, which is set forth in the above item (1), wherein the filtering member is formed of a laminate comprising a plurality of porous bodies, the whole or a part of the laminate is provided with a gradient of the porosity.

(3) The apparatus for isolating and recovering an objective cell, which is set forth in the above item (1) or (2), wherein the first line is also employed as a line for feeding a recovery liquid for recovering the objective cell.

(4) The apparatus for isolating and recovering an objective cell, which is set forth in any one of the above items (1) to (3), wherein the storage container is also employed as a container for recovering the objective cell.

(5) The apparatus for isolating and recovering an objective cell, which is set forth in any one of the above items (1) to (4), wherein the apparatus further comprises a fourth line provided with a waste liquid container for storing the liquid to be treated which has been passed through the filtering device.

(6) The apparatus for isolating and recovering an objective cell, which is set forth in any one of the above items (1) to (5), wherein at least one of the first line, the second line and the third line is provided with opening/closing means for opening or closing the passage of the liquid.

(7) The apparatus for isolating and recovering an objective cell, which is set forth in any one of the above items (1) to (6), wherein the apparatus further comprises a first connector provided with a branched tube having two branches which form an acute angle and are connected respectively with the second line and with the third line.

(8) The apparatus for isolating and recovering an objective cell, which is set forth in the above item (7), wherein the first connector is formed of a ⊦-shaped or a Y-shaped tube.

(9) The apparatus for isolating and recovering an objective cell, which is set forth in any one of the above items (1) to (8), wherein the apparatus comprises a second connector provided with a branched tube having two branches which form an acute angle and are connected respectively with the first line and with a line communicated with the filtering device.

(10) The apparatus for isolating and recovering an objective cell, which is set forth in the above item (9), wherein the second connector is formed of a ⊦-shaped or a Y-shaped tube.

(11) A method of isolating and recovering an objective cell by using a filtering member composed of a porous body whose porosity can be changed, the method comprising the steps of;
performing a priming wherein a filtering member is impregnated with a priming liquid;
isolating the objective cell by passing a liquid to be treated through the filtering member under a condition where the porosity of the filtering member is set to a first porosity which enables the objective cell to be captured, thereby performing the isolation of the objective cell;
washing the filtering member by causing an excessive quantity of the priming liquid which has passed through the filtering member to pass again through the filtering member; and
recovering the objective cell captured in the filtering member by causing a recovery liquid to pass through the filtering member under a condition where the porosity of the filtering member is set to a second porosity which is larger than the first porosity.

(12) A method of isolating and recovering an objective cell by using an apparatus which comprises a filtering member composed of a porous body and capable of changing the porosity thereof, a first line for feeding a priming liquid to the filtering member, and a second line for feeding a liquid to be treated containing the objective cell to the filtering member; the method comprising the steps of;
performing a priming by feeding the priming liquid through the first line thereby impregnating the filtering member with the priming liquid, while allowing an excessive quantity of the priming liquid that has passed through the filtering member to be stored in a storage container;
isolating the objective cell by feeding the liquid to be treated through the second line so as to pass the liquid through the filtering member under a condition where the porosity of the filtering member is set to a first porosity which enables the objective cell to be captured, thereby performing the isolation of the objective cell;
washing the filtering member by causing the priming liquid which has been stored in the storage container during the priming step to pass again through the filtering member; and
recovering the objective cell captured in the filtering member by causing a recovery liquid to pass through the filtering member under a condition where the porosity of the filtering member is set to a second porosity which is larger than the first porosity.

(13) The method of isolating and recovering an objective cell, which is set forth in the above item (12), wherein the washing step includes also a washing of the second line.

(14) The method of isolating and recovering an objective cell, which is set forth in the above item (12) or (13), wherein a sequence of the steps are performed in a closed system.

(15) The method of isolating and recovering an objective cell, which is set forth in any one of the above items (11) to (14), wherein the direction of the priming liquid passing through the filtering member in the priming step is reverse from the direction of the liquid to be treated passing through the filtering member.

(16) The method of isolating and recovering an objective cell, which is set forth in any one of the above items (11) to (15), wherein the direction of the priming liquid passing through the filtering member in the priming step is the same as the direction of the liquid to be treated passing through the filtering member.

(17) The method of isolating and recovering an objective cell, which is set forth in any one of the above items (11) to (16), wherein the direction of the priming liquid passing through the filtering member in the priming step is reverse from the direction of the priming liquid passing through the filtering member in the washing step.

(18) The method of isolating and recovering an objective cell, which is set forth in any one of the above items (11) to (17), wherein the direction of the priming liquid passing through the filtering member in the washing step is reverse from the direction of the recovery liquid passing through the filtering member.

(19) A method of isolating and recovering an objective cell by using the apparatus set forth in any one of the above items (1) to (10), the method comprising the steps of;
 impregnating the filtering member of the isolating and recovering apparatus with a priming liquid;
 isolating the objective cell by passing a liquid to be treated through the filtering member under a condition where the porosity of the filtering member is set to a first porosity which enables the objective cell to be captured;
 causing an excessive quantity of the priming liquid which has passed through the filtering member to pass again through the filtering member; and
 recovering the objective cell by causing a recovery liquid to pass through the filtering member under a condition where the porosity of the filtering member is set to a second porosity which is larger than the first porosity.

(20) The method of isolating and recovering an objective cell, which is set forth in any one of the above items (12) to (19), wherein the recovery liquid is fed through the first line.

(21) The method of isolating and recovering an objective cell, which is set forth in any one of the above items (12) to (20), wherein the objective cell is recovered in the storage container.

(22) The method of isolating and recovering an objective cell, which is set forth in any one of the above items (11) to (21), wherein a degassing operation to remove air bubble from the filtering member is performed during a period between the initiation of the priming and the initiation of the isolation of the objective cell.

(23) The method of isolating and recovering an objective cell, which is set forth in the above item (22), wherein the degassing operation is performed by changing the compression ratio of the filtering member a plurality of times thereby changing the porosity of the filtering member a plurality of times.

(24) The method of isolating and recovering an objective cell, which is set forth in any one of the above items (11) to (23), the method further comprising a detaching operation to promote the release of the objective cell from the filtering member by causing instantaneous change of the direction and/or flow rate of the recovery liquid at and around the filtering member in the middle of recovering the objective cell.

(25) The method of isolating and recovering an objective cell, which is set forth in the above item (24), wherein the detaching operation is performed by changing the compression ratio of the filtering member a plurality of times, thereby changing the porosity of the filtering member a plurality of times.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
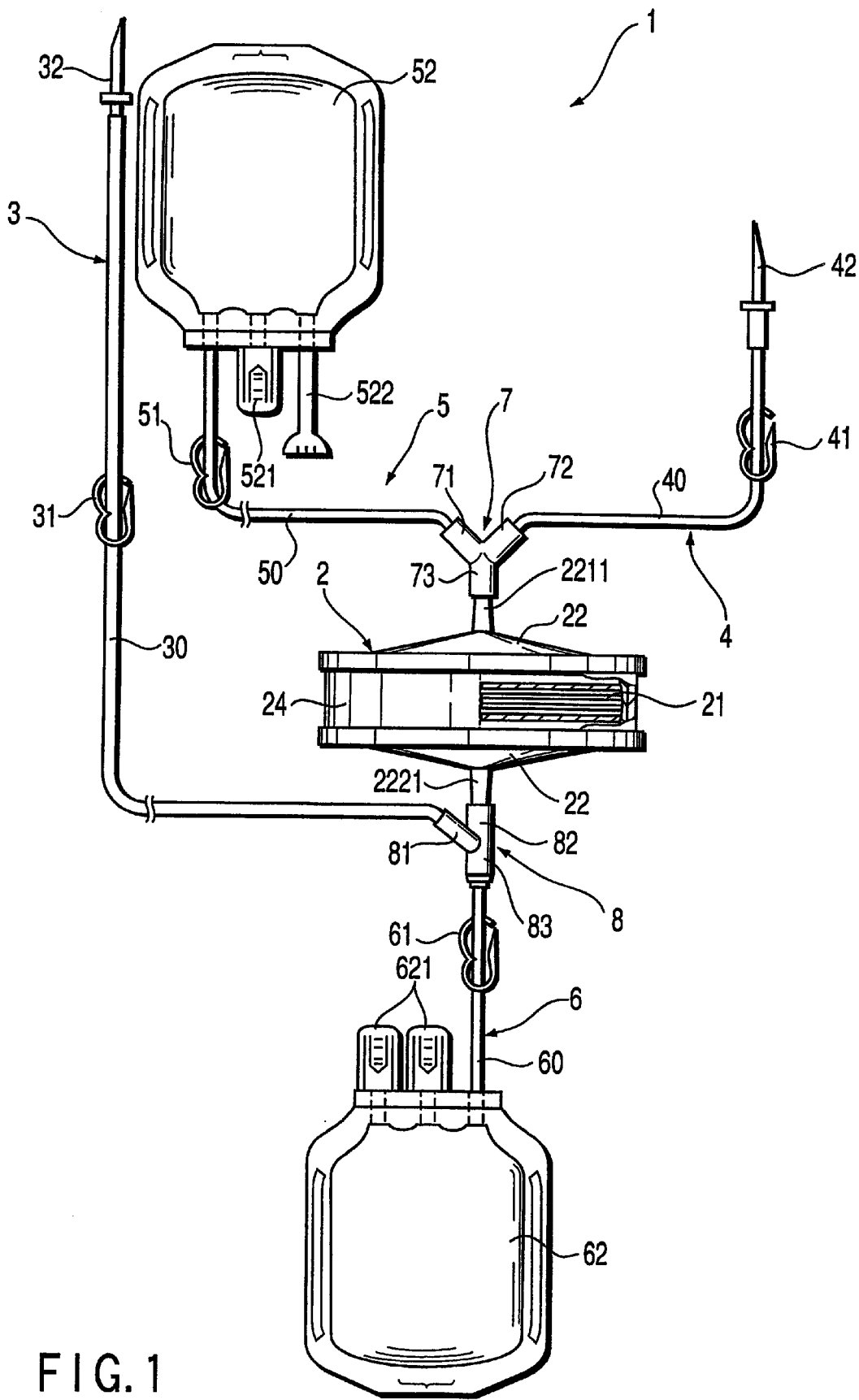
FIG. 1 represents a circuit diagram illustrating one embodiment of the cell isolating and recovering apparatus according to the present invention.

This invention will be further illustrated with reference to preferable embodiments shown in the drawings.

FIG. 1 represents a circuit diagram illustrating one embodiment of the cell isolating and recovering apparatus according to this invention.

The cell isolating and recovering apparatus according to this invention comprises a filtering device 2; a first line 3 for feeding a priming liquid to the filtering device 2; a second line 4 for feeding a liquid to be treated containing the objective cell intended to be isolated to the filtering device 2; a third line 5 provided with a storage container 52 for storing the priming liquid that has been passed through the filtering device 2; a fourth line 6 for discharging a waste liquid such as the liquid to be treated that has passed through the filtering device 2; a first connector 7 for connecting the second line 4 and the third line 5 so as to communicate them with the filtering device 2; and a second connector 8 for connecting the first line 3 and the fourth line 6 so as to communicate them with the filtering device 2.

One end (a first port 2211 to be illustrated hereinafter) of the filtering device 2 is connected with a third branch tube 73 of the first connector 7, and the other end (a second port 2221 to be illustrated hereinafter) of the filtering device 2 is connected with a second branch tube 82 of the second connector 8.

This filtering device 2 is designed to capture an objective cell intended to be isolated and recovered (hereinafter referred to as "objective cell") from a liquid to be treated which will be described hereinafter, and to release the objective cell thus captured therein.

Figure 2:
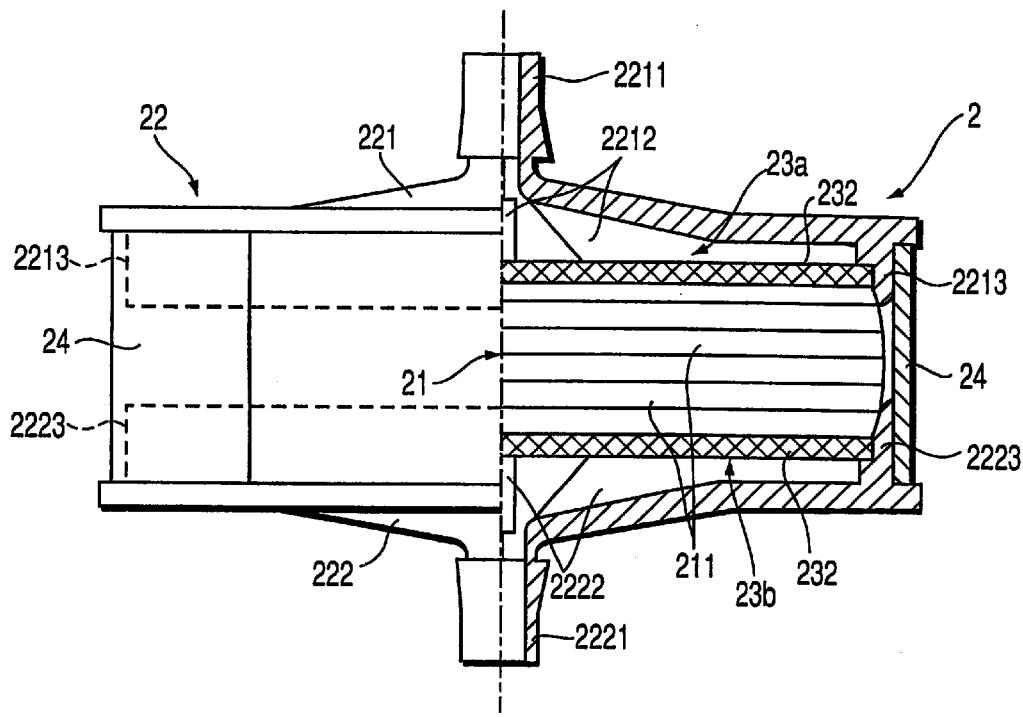
FIG. 2 is a partially sectioned side elevation view illustrating the filtering device shown in FIG. 1.
Figure 3:
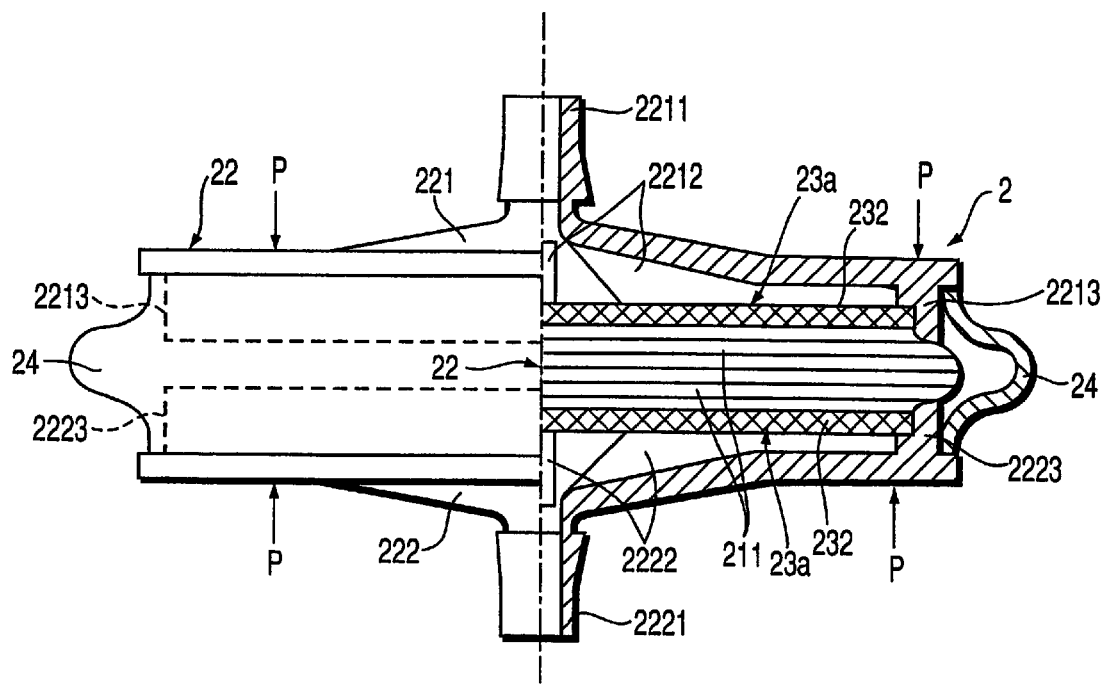
FIG. 3 is a partially sectioned side elevation view illustrating the filtering device shown in FIG. 1.

As shown in FIGS. 2 and 3, the filtering device 2 is composed of a housing 22, a filtering member 21 placed in the housing 22, flow passage-securing members 23a and 23b, and a sealing member 24.

The filtering member 21 is formed of a laminate consisting of a plurality of porous polymer membranes 211. Each porous polymer membrane 211 is preferably made of an elastic material which is hardly capable of being plastically deformed by an external force such as compression or extension and is capable of restoring it original configuration as the external force is removed. Specific examples of the porous polymer membrane 211 are a porous body of high molecular materials such as polyurethane, styrene-butadiene rubber, polyvinyl alcohol, polypropylene, polyether polyamide, etc.

When the filtering member 21 is in a compressed state as a predetermined compressive force is applied to the filtering member 21 as shown in FIG. 3, each porous polymer membrane 211 of the filtering member 21 according to this embodiment is compacted or densified, so that the porosity of each porous polymer membrane 211 becomes a first porosity which is lower in porosity than a second porosity to be described hereinafter. This first porosity is suited for capturing and isolating the objective cell.

On the other hand, when the filtering member 21 is in a state where no compressive force is applied to the filtering member 21, in a state where the compressive force is relieved, or in a state where the compressive force is alleviated as shown in FIG. 2, the porosity of each porous polymer membrane 211 takes a second porosity which is suited for releasing the objective cell that has been captured by the filtering member 21.

The ratio of the second porosity to the first porosity in this case may be suitably determined depending on the various conditions such as the types and size of the objective cell. In general, however, the second porosity should preferably be about 1.05 to 3 times, more preferably about 1.10 to 2.0 times as high as the first porosity. If the ratio of the second porosity to the first porosity is smaller than this lower limit, there is a possibility that the effect of improving the yield of the objective cell through the alteration of porosity may not be sufficiently achieved, depending on the types and size of the objective cell. On the other hand, if the ratio of the second porosity to the first porosity exceeds over this upper limit, the first porosity becomes lower than 33%, so that the passage of the liquid to be treated containing the objective cell through the porous polymer membrane 211 may be badly deteriorated.

If the average pore diameter of the filtering member 21 in the compressed state is defined as a first pore size, and if the average pore size of the filtering member 21 in the compression force-relieved state is defined as a second pore size, these first pore size and second pore size may be suitably determined depending on various conditions such as the types and size of the objective cell. For example, when the objective cell is lymphocyte, the first pore size should preferably be less than 5 $\mu$m, more preferably in the range of 2 to 4.9 $\mu$m, while the second pore size should preferably be not less than 5 $\mu$m, more preferably not less than 6 $\mu$m.

Although the filtering member 21 may be formed of a plurality of the same porous polymer membranes 211, it is more preferable that porous polymer membranes 211 constituting the filtering member 21 has a gradient in physical or chemical properties, or especially, all or some of the porous polymer membranes 211 are provided with different physical or chemical properties from the other porous polymer membranes 211. It is possible due to this difference in physical or chemical properties to enhance the capturability of the objective cell and/or the releasability of the objective cell on the occasion of the recovering.

The physical or chemical properties to be provided with a gradient can be suitably determined based on a condition such as the type, size and property of the objective cell, so that the capturability of the objective cell by the filtering member and/or the releasability of the objective cell on the occasion of the recovery can be improved due to the provision of this gradient.

The gradient is realized by, for example, a structure in which the porous polymer membrane are stacked in such a manner that at least any one of the porosity, average pore diameter, zeta-potential and hydrophilicity is changed continuously or stepwise in the direction along which the liquid to be treated are allowed to flow.

As for the laminated structure wherein the porosity is gradually changed, use may be made of the construct in which the porous polymer membranes 211 are laminated so as to cause the porosity to become gradually smaller in the direction from the first port 2211 side to the second port 2221 side as described hereinafter.

As for the laminated structure wherein the average pore diameter is gradually changed, it is possible to employ such a construct that the porous polymer membranes 211 are laminated so as to cause the average pore diameter to become gradually smaller in the direction from the first port 2211 side to the second port 2221 side as described hereinafter.

In order to achieve the laminated structure wherein the zeta-potential is gradually changed, it is possible to employ a method of successively laminating the porous polymer membranes 211 so as to cause the zeta-potential to become gradually increased, in particular to cause the zeta-potential to change from negative to positive, in the direction from the first port 2211 side to the second port 2221 side as described hereinafter.

As for the laminated structure wherein the hydrophilicity is gradually changed, a method of successively laminating the porous polymer membranes 211 so as to cause the hydrophilicity to become gradually enhanced in the direction from the first port 2211 side to the second port 2221 side may be adopted.

The directivity or orientation of these gradients is not limited to the aforementioned examples, but may be optionally altered depending on the types of objective cell.

The filtering member 21 is provided on both surfaces thereof with the flow passage securing members 23a and 23b, respectively, and is placed together with these flow passage securing members 23a and 23b in the housing 22. Each of the flow passage securing members 23a and 23b is constituted by a polycarbonate spacer 232 having through-holes for preventing the spacer 232 from being distorted on the occasion of compression for instance, and by a mesh (not shown) which is interposed between the spacer 232 and the filtering member 21.

With the provision of the flow passage securing member 23a, a space communicating with the first port 2211 is secured on the inside of the rib 2212 to be explained hereinafter, thereby securing a passageway through which the liquid entering from the first port 2211 can flow toward the filtering member 21. On the other hand, with the provision of the flow passage securing member 23b, a space communicating with the second port 2221 is secured on the inside of the rib 2212, thereby securing a passageway through which the liquid entering from the second port 2221 can flow toward the filtering member 21. Namely, the filtering member 21 is mounted inside the housing 22 in such a manner as to partition the housing 22 into a space communicating with the first port 2211 and a space communicating with the second port 2221.

Since a mesh (not shown) is interposed between the spacer 232 and the filtering member 21 in the flow passage securing members 23a and 23b, the liquid passing through the inner space of the rib 2212 can be uniformly dispersed all over the filtering member 21, thus making it possible to enhance the efficiency in the filtration, washing and recovery of the objective cell.

The housing 22 is composed of a first housing member 221 and a second housing member 222, which are formed symmetrical with each other.

The first housing 221 is provided at the center thereof with a projected first port 2211 communicating with the interior of the housing 22 and constituting an inflow port for liquid to be treated. Likewise, the second housing 222 is provided at the center thereof with a projected second port 2221 communicating with the interior of the housing 22 and constituting a filtrate outflow port.

The first housing 221 is also provided therein with a plurality of plate-like ribs 2212 pressing the flow passage securing member 23a for compressing the filtering member 21. Likewise, the second housing 22 is also provided therein with a plurality of plate-like ribs 2222 pressing the flow passage securing member 23b for compressing the filtering member 21. These plurality of plate-like ribs 2212 and 2222 are respectively formed radially extending from the central axis of the housing 22.

The upper inner wall of the first housing 221 is converged toward the first port 2211 thereby forming a funnel-like configuration, thus enabling air bubble to float upward along this funnel-like inner wall on the occasion of priming to be explained hereinafter, and improving the discharge of the air bubble.

Likewise, the lower inner wall of the second housing 222 is converged toward the second port 2221 thereby forming a funnel-like configuration, thus smoothing the liquid flow inside the housing 22, in particular, enabling the liquid to be smoothly discharged from the second port 2221.

The first housing 221 is also provided at the outer peripheral portion thereof with an annular rib 2213 for fixing a sealing member 24 in place. Likewise, the second housing 222 is also provided at the outer peripheral portion thereof with an annular rib 2223 for fixing the sealing member 24 in place. These annular ribs 2213 and 2223 are extended to face to each other.

Namely, the housing 22 is provided at the outer peripheral portion thereof with a cylindrical sealing member 24. This sealing member 24 is formed of an elastic material such as rubber of various types or a thermoplastic elastomer and is adhered or fuse-bonded through the opposite end portions thereof (in the axial direction thereof) to the annular ribs 2213 and 2223, thus liquid-tightly fixing the sealing member 24 to the housing 22.

These annular ribs 2213 and 2223 are designed to strongly press the peripheral portion of each porous polymer membrane 211 when the filtering member 21 is in a compressed state. Therefore, when the filtering member 21 is in a compressed state, the liquid to be treated passing through the filter device 2 is inhibited from passing beyond the annular ribs 2213 and 2223 to the outer periphery of the filtering member 21.

When the filtering member 21 is a non-compressed state as shown in FIG. 2, the sealing member 24 is kept approximately in a cylindrical configuration. However, when a compression force P is applied to the housing 22, the filtering member 21 is turned into a compressed state as shown in FIG. 3, thereby causing a middle portion (in the axial direction) of the sealing member 24 to become deformed or protruded externally.

By mounting the sealing member 24 in this manner, the liquid-tightness and in particular, the asepsis of the housing 22 is ensured irrespective of the compressed or non-compressed state of the filtering member 21.

The configuration of the sealing member 24 is not limited to that shown in these FIGS., but may be of a bellows-like configuration. Further, the sealing member 24 may be fixed inside the annular ribs 2213 and 2223.

In this filter device, it is possible to change, as required, the compression force P applied to the housing 22 so as to change the compressed condition and hence, the porosity of the filtering member 21, by making use of a porosity-changing means (not shown).

As for this porosity-changing means, a mechanism comprising a pair of pressing members which can be moved close to each other or spaced apart from each other through the movement of at least one of the pressing members, and means for driving the pressing members to move as mentioned above can be employed for instance.

The filter device 2 is interposed between these pressing members of the porosity-changing means, and then, these pressing members are moved close to each other, thus applying a compression force P to the housing 22 of the filter device 2, thereby compressing the filtering member 21 placed inside the housing 22.

Then, by moving these pressing members away from each other, the compression force P that has been applied to the housing 22 can be relieved, thereby relieving the compression of the filtering members 21 placed inside the housing 22.

Next, the connectors to be connected with the filter device 2 and each line to be connected with each connector will be explained.

A first line 3 is composed of a first tube 30, a first clamp 31 and a first bottle-puncturing needle 32. One end of the first tube 30 is connected with a first branch tube 81 of the second connector 8, and the other end of the first tube 30 is connected with the first bottle-puncturing needle 32.

The first bottle-puncturing needle 32 is designed to pierce into an elastic plug of a container in which a priming liquid (not shown) is stored (hereinafter referred to as a priming liquid-storage container), thereby connecting the first line 3 with the priming liquid-storage container. As a result, it is now possible to feed a priming liquid to be impregnated in the filtering member 21 of the filter device 2, from the priming liquid-storage container, via the first bottle-puncturing needle 32, the first tube 30 and the second connector 8, to the filter device 2.

Further, on the occasion of recovering an objective cell, a recovery liquid for recovering the objective cell captured by the filter device 2 can be fed from the priming liquid-storage container, via the first bottle-puncturing needle 32, the first tube 30 and the second connector 8, to the filter device 2.

Namely, the first line 3 is capable of not only feeding a priming liquid to the filter device 2 but also feeding a recovery liquid to the filter device 2.

The first tube 30 is formed of a material which is excellent in flexibility and pliability, suited to be closed or opened by means of a clamp, and also suited for sterilization, a specific example thereof being soft polyvinyl chloride.

A second tube 40, a third tube 50 and a fourth tube 60 which will be explained below are also formed of the same kind of material as that of the first tube 30.

As for the priming liquid, there is no particular limitation as long as the filtering member 21 of the filter device 2 can be impregnated with the priming liquid. For example, a physiological saline; a buffer solution such as a phosphate buffer and a citrate buffer; a culture liquid; a specific gravity liquid; a plasma expander; or any one of these liquids to which albumin or plasma is added can be employed. When a liquid to be treated is blood as described hereinafter, the priming liquid should preferably be selected from those having composition which are close to those of plasma. Preferable examples thereof are a physiological saline, a phosphate buffer, a culture liquid, and any one of these liquids to which albumin or plasma is added.

As for the recovery liquid, there is no particular limitation as long as it is capable of recovering an objective cell from the filter device 2. For example, a liquid which is similar in composition to the priming liquid, or a cryoprotective liquid can be employed.

If the objective cell is lymphocyte or hematopietic stem/progenitor cell, the recovery liquid should preferably be a liquid which contains albumin, such as an albumin-containing physiological saline. Because when albumin is included in a recovery liquid, the release of lymphocyte or hematopietic stem/progenitor cell from the filtering member 21 can be facilitated.

It is preferable that a recovery liquid is the same type as a priming liquid. If a recovery liquid is formulated in this manner, the priming liquid stored in the priming liquid storage container can be employed as a recovery liquid by simply operating the first clamp 31 as explained hereinafter. Namely, the priming liquid storage container can be employed also as a container for feeding a recovery liquid.

The first tube 30 is provided at the intermediate portion thereof with a first clamp 31 as means for opening or closing the passage of liquid therethrough.

Through the manipulation of this first clamp 31, the first tube 30 can be closed or opened so as to introduce a required volume of the priming liquid or recovery liquid into the first tube 30 as required. Further, by closing the first tube 30 by means of this first clamp 31, the liquid to be treated which will be explained later can be prevented from flowing into the other end of the first tube 30, i.e. toward the first bottle-puncturing needle 32.

The third line 5 is composed of a third tube 50, a third clamp 51 and a storage container 52. One end of the third line 5 is connected with a first branch tube 71 of the first connector 7. The other end of the third tube 50 is connected with a storage container 52.

When a priming liquid is fed to the filter device 2, the priming liquid is allowed to enter into the filter device 2 from the second port 2221, thus filling the interior of the housing 22 with the priming liquid, and impregnating the filtering member 21 with the priming liquid. When the feeding of the priming liquid to the housing 22 is further continued, the excessive amount of the priming liquid overflows from the first port 2211, thus causing the excessive amount of the priming liquid to pass through the third tube 50 into the storage container 52, and allowing the priming liquid to be stored in the storage container 52.

This excessive amount of the priming liquid stored in the storage container 52 is then employed as a washing liquid on the occasion of washing the filter device 2. Further, this storage container 52 is also capable of recovering therein a recovery liquid passed through the filter device 2 and containing an objective cell. Namely, this storage container 52 is designed in such a manner that it is capable of not only storing an excessive quantity of priming liquid but also recovering a recovery liquid containing an objective cell.

Therefore, the third tube 50 acts not only as a passageway for introducing an excessive quantity of priming liquid that has been flown out of the first port 2211 into the storage container 52, but also as a passageway for feeding a washing liquid to the filter device 2. Further, the third tube 50 can be used also as a passageway for a recovery liquid passed through the filter device 2 and containing an objective cell.

After the filtering member 21 is impregnated with a priming liquid, an excessive quantity of the priming liquid that has flown out of the first port 2211 can be employed subsequently as a washing liquid, thereby making it unnecessary to newly prepare a washing liquid for washing the filter device 2.

Since the cell-isolating and recovering apparatus 1 is no more required to provide it with an inlet port for introducing a washing liquid, it can be more simplified in construction as compared with the conventional apparatus and can be manufactured at lower cost as compared with the conventional apparatus.

The storage container 52 is formed of a bag made of a flexible soft resin sheet, such as a polyvinyl chloride sheet, whose peripheral portions are overlapped and adhered or fusion-bonded with each other so as to form the bag.

The storage container 52 is provided at the upper periphery thereof with an opening portion 521 consisting of a short tube having a sealed distal end and covered entirely with a case sheet which is openable by a peel tub. Namely, this short tube can be exposed by pulling the peel tub to open the case sheet. When this exposed short tube is communicated with a needle tube by piercing the needle tube into the short tube, it is possible to perform the sampling of a recovery liquid containing an objective cell from the storage container 52. The recovering liquid thus sampled is then subjected to various kinds of test and analysis such as virus check and the functional assay of cell.

The storage container 52 is further provided at the upper periphery thereof with a recovery liquid-withdrawing tube 522. The distal end of this recovery liquid-withdrawing tube 522 is sealed by means of fusion bond for instance. This recovery liquid-withdrawing tube 522 can be sterilely connected with another tube by making use of a sterile tube-connecting device (Japanese Utility Model Unexamined Publication H6-26877), thereby making it possible to transfer the recovery liquid stored in the storage container 52 to a separate container communicated with said another tube through this connection between the recovery liquid-withdrawing tube 522 and said another tube.

The third tube 50 is provided at the intermediate portion thereof with a third clamp 51 as means for opening or closing the passage of liquid through the tube.

Through the manipulation of this third clamp 51, the third tube 50 can be closed or opened so as to introduce a washing liquid into the third tube 50 as required. It is also possible to introduce a recovery liquid into the storage container 52 in the same manner as mentioned above. Further, by closing the third tube 50 by means of this third clamp 51, the liquid to be treated can be prevented from flowing into the storage container 52.

The second line 4 is composed of a second tube 40, a second clamp 41 and a second bottle-puncturing needle 42. One end of the second tube 40 is connected with a second branch tube 72 of the first connector 7. The other end of the second tube 40 is connected with the second bottle-puncturing needle 42.

The second line 4 can be connected with a container (not shown) in which a liquid to be treated is stored (hereinafter referred to as a storage container of liquid to be treated) by piercing the second bottle-puncturing needle 42 into an elastic plug of the storage container of liquid to be treated. As a result, the liquid to be treated containing an objective cell for isolation can be fed from the storage container to the filter device 2, via the second bottle-puncturing needle 42, the second tube 40 and the first connector 7.

As for the liquid to be treated which is applied to the cell-isolating and recovering apparatus 1, there is no particular limitation as long as it contains an objective cell that can be isolated by the filter device 2. For example, body fluids such as blood, lymph, cerebrospinal fluid and cord blood; a treated body fluid such as a blood component (such as plasma and buffy coat); and a suspension of cell may be employed.

As for the objective cell, a cell such as lymphocyte (entire cells of lymphocyte or a specific type thereof) or hematopietic stem/progenitor cell may be applicable to in this invention. The cell in this invention includes not only the aforementioned cells but also living microorgan tissues such as cell nucleus, chromosome, chromatin, cell membrane structure, organelle, etc.

The second tube 40 is provided at the intermediate portion thereof with a second clamp 41 as means for opening or closing the passage of liquid through the tube.

By manipulating of this second clamp 41, the second tube 40 can be closed or opened so as to introduce a required volume of a liquid to be treated into the second tube 40 as required. Further, by closing the second tube 40 by means of this second clamp 41, the priming liquid, the washing liquid as well as the liquid to be treated can be prevented from flowing toward the other end of the second tube 40, i.e. toward the second bottle-puncturing needle 42.

If required, a filtering material such as mesh, woven fabric, nonwoven fabric, filter paper may be disposed in the middle portion or at the end portion of the second line 4. It is possible, with this provision of such a filtering material, to remove in advance (i.e. before the liquid to be treated is filtered in the filter device 2) any coagulated matters in the liquid, thus preventing the filtering member 21 of the filter device 2 from being clogged with a coagulate, and hence, improving the filtration efficiency.

The fourth line 6 is composed of a fourth tube 60, a fourth clamp 61 and a waste liquid container 62. One end of the fourth tube 60 is connected with a third branch tube 83 of the second connector 8. The other end of the fourth tube 60 is connected with the waste liquid container 62.

The liquid to be treated or washing liquid that has passed through the filter device 2 is transferred via the fourth tube 60 to the waste liquid container 62 and stored therein.

The waste liquid container 62 is formed of a bag made of a flexible soft resin sheet, such as a polyvinyl chloride sheet, whose peripheral portions are overlapped and adhered or fusion-bonded with each other so as to form the bag.

The waste liquid container 62 is provided at the upper periphery thereof with a pair of opening portions 621 each consisting of a short tube having a sealed distal end and covered entirely with a case sheet which is openable by a peel tub. Namely, each of these short tubes can be exposed by pulling the peel tub to open the case sheet. Each exposed short tube can be communicated with a needle tube by piercing the needle tube into the short tube, thus making it possible to perform the sampling or withdrawing of treated liquid, etc. that has been passed through the filter device 2 and stored in the waste liquid container 62. The treated liquid thus sampled can be then subjected to various kinds of assay and analysis such as virus check.

The fourth tube 60 is provided at the intermediate portion thereof with a fourth clamp 61 as means for opening or closing the passage of liquid through the tube.

By manipulating this fourth clamp 61, the fourth tube 60 can be closed or opened so as to transfer, as required, a liquid that has been passed through the filter device 2 into the waste liquid container 62. Further, by closing the fourth tube 60 by means of this fourth clamp 61, the priming liquid or the recovery liquid that has been supplied from the first tube 30 can be prevented from flowing into the waste liquid container 62, thereby making it possible to feed the priming liquid or the recovery liquid to the filter device 2.

The first connector 7 is formed of a Y-shaped tube consisting of a first branch tube 71, a second branch tube 72 and a third branch tube 73. The first branch tube 71 is connected with the third tube 50, the second branch tube 72 is connected with the second tube 40, and the third branch tube 73 is connected with the first port 2211 of the filter device 2.

As shown in FIG. 1, the first branch tube 71 and the second branch tube 72 are angled from each other at an acute angle (at an angle of not more than 90 degrees).

When the third line 5 and the second line 4 are connected with each other at the acute angle defined by the first branch tube 71 and the second branch tube 72, the liquid to be treated which is fed from the second tube 40 to the filter device 2 is inhibited from entering into the third tube 50. When the liquid to be treated is inhibited from entering into the third tube 50 in this manner, it becomes possible to reduce the amount of the components of the liquid that may be adhered onto the inner wall of the third tube 50, thus making it possible to inhibit unwanted components from entering into the recovery liquid on the occasion of recovering an objective cell into the storage container 52.

In particular, when the liquid to be treated is of high viscosity such as blood or plasma, the liquid can be further inhibited from flowing into the third tube 50 due to the acute angle at which the second line 4 and the third line 5 are connected together. On the other hand, when the washing liquid is of low viscosity such as physiological saline, the washing liquid can be easily introduced into the second tube 40 from the third tube 50.

Although the third branch tube 73 is directly connected with the first port 2211 in the embodiment shown in the drawings, they can be connected with each other through a tube.

The second connector 8 is formed of an ⊦-shaped tube consisting of a first branch tube 81, a second branch tube 82 and a third branch tube 83. The first branch tube 81 is connected with the first tube 30, the second branch tube 82 is connected with the second port 2221 of the filter device 2

(the line communicating with the filter device 2), and the third branch tube 83 is connected with the fourth tube 60.

As shown in FIG. 1, the first branch tube 81 and the second branch tube 82 are angled from each other at an acute angle (at an angle of not more than 90 degrees).

When the first tube 30 and the second port 2221 of the filter device 2 are connected with each other at the acute angle defined by the first branch tube 81 and the second branch tube 82, the treated liquid fed from the filter device 2 to the fourth tube 60 is inhibited from entering into the first tube 30. When the treated liquid is inhibited from entering into the first tube 30 in this manner, it becomes possible to reduce the amount of the components of the treated liquid that may be adhered onto the inner wall of the first tube 30, thus making it possible to inhibit unwanted components from entering into the recovery liquid on the occasion of recovering an objective cell into the storage container 52.

In particular, when the liquid to be treated is of high viscosity such as blood or plasma, the treated liquid can be further inhibited from flowing into the first tube 30 due to the acute angle at which the first line 3 and the line communicating with the filter device 2 are connected together. On the other hand, when the priming liquid or the recovery liquid is of low viscosity such as physiological saline, these liquids can be easily introduced into the filter device 2 from the first tube 30.

Although the second branch tube 82 is directly connected with the second port 2221 in the embodiment shown in the drawings, they can be connected with each other through a tube.

Now, one example of using the cell-isolating and recovering apparatus 1 will be explained as follows.

First of all, the first bottle-puncturing needle 32 is pierced into a priming liquid storage container, and then, the second bottle-puncturing needle 42 is pierced into a storage container of liquid to be treated.

As a result, the first line 3 is connected with the priming liquid storage container, and the second line 4 is connected with the storage container of the liquid to be treated.

Since the first line 3 and the second line 4 are connected with the priming liquid storage container and the storage container of the liquid to be treated, respectively, the cell-isolating and recovering apparatus 1 constitutes a closed system, thus making it possible to perform the following steps in the closed system. Therefore, an objective cell can be isolated and recovered aseptically.

In each of the following operations, the priming liquid, the liquid to be treated, the washing liquid and the recovery liquid were all caused to naturally flow under the gravitation thereof.

In this case, the cell-isolating and recovering apparatus 1 should preferably be set such that the filter device 2 is disposed at higher level than that of the waste liquid container 62, that the storage container of the liquid to be treated is disposed at higher level than that of the filter device 2, that the storage container 52 is disposed at higher level than that of the container of the liquid to be treated, and that the priming liquid storage container is disposed at higher level than that of the storage container 52. Namely, the cell-isolating and recovering apparatus 1 should preferably be set such that the priming liquid storage container, the storage container 52, the storage container of the liquid to be treated, the filter device 2 and the waste liquid container 62 are arranged at the levels which become lower in the mentioned order.

In this case, it is further preferable, in view of promoting the removal of air bubble through the floatup thereof, to set the filter device 2 in such a manner that the first port 2211 thereof is extended perpendicularly upward, and the second port 2221 is extended perpendicularly downward.

When the cell-isolating and recovering apparatus 1 is arranged in this manner, the priming liquid, the liquid to be treated, the washing liquid and the recovery liquid can be suitably transferred by simply manipulating the opening and closing of the first, second, third and fourth clamps.

In each of the following manipulations, the opening and closing of the first, second, third and fourth clamps are performed concurrent with the compression and the loosening of the filtering member 21. These opened and closed patterns as well as these compression and loosening patterns are shown in the following Table 1.

TABLE 1

|  | First clamp 31 | Second clamp 41 | Third clamp 51 | Fourth clamp 61 | Filtering member 21 |
| --- | --- | --- | --- | --- | --- |
| [1]Priming 1 | ○ | x | ○ | x | Loosened |
| [2]Priming 2 | x | ○ | ○ | x | Loosened |
| [3]Filter compressed | x | x | ○ | x | Compressed |
| [4]Filtration 1 | x | ○ | x | ○ | Compressed |
| [5]Washing 1 | x | ○ | ○ | x | Compressed |
| [6]Filtration 2 | x | ○ | x | ○ | Compressed |
| [7]Washing 2 | x | x | ○ | ○ | Compressed |
| [8]Filter loosened | ○ | x | x | x | Loosened |
| [9]Recovering | ○ | x | ○ | x | Loosened |

○: Opened
x: Closed

[1] First of all, the filtering member 21 is loosened, i.e. the filter device 2 is kept free from any compressive force, and then, the first, second, third and fourth clamps are set to the opened and closed patterns as shown in Table 1.

Under this condition, the priming liquid is allowed to be transferred from the priming liquid storage container, via the first bottle-puncturing needle 32, the first tube 30 and the second connector 8, to the filter device 2.

The priming liquid fed to the filter device 2 is then introduced from the second port 2221 into the interior of the filter device 2. As a result, the air inside the filter device 2 is replaced by the priming liquid and hence, the filter device is filled with the priming liquid.

As a result, the filtering member 21 inside the filter device 2 is impregnated with the priming liquid.

When the priming liquid is fed further to the interior of the filter device 2, the priming liquid begins to be overflowed from the first port 2211 of the filter device 2, and an excessive volume of priming liquid thus overflowed is allowed to pass through the first connector 7 and the third tube 50 into the storage container 52, and stored therein.

During this priming operation, the priming liquid is allowed to pass through the filter device 2 from the lower side of the filter device 2 to the upper side thereof as viewed in FIG. 1.

When the interior of the filter device 2 is filled with the priming liquid, the filtering member 21 is caused to swell, thus turning the filtering member 21 into a suitable condition for a liquid to be treated can pass through the filter member 21.

Further, when the air inside the filter device 2 is replaced by the priming liquid, the passageway for the liquid to be treated, the washing liquid and the recovery liquid can be secured in the filter device, thus permitting these liquids to smoothly pass through the filtering member 21.

It is preferable in this manipulation to allow the priming liquid to pass perpendicularly through the filter device 2 from the lower side of the filter device 2 to the upper side thereof. By causing the priming liquid to pass perpendicularly through the filter device 2 from the lower side of the filter device 2 to the upper side thereof, it becomes possible to promote the float-up of air bubble, thus minimizing the residual ratio of air bubble in the filter device 2.

It is preferable to perform a de-gassing operation during the time in which the priming liquid is allowed to pass through the filter device 2. As a result of this de-gassing operation, the removal of air bubble inside the filtering member 21 can be promoted, thus substantially increasing the effective area of the filtering member 21, and hence, allowing the liquid to be treated, the washing liquid and the recovery liquid to smoothly and effectively pass through the filtering member 21. Accordingly, by the employment of this de-gassing operation, the filtration time for the liquid to be treated to pass through the filtering device 2 can be shortened, thus improving the recovery ratio of objective cell.

This de-gassing operation can be performed by a method where the compression ratio of the filtering member 21 is changed once or a plurality of times. More specifically, the de-gassing operation can be performed by repeating a plurality of times the compression (the application of compressive force) and loosening (release of compressive force) of the filtering member 21 (hereinafter referred to as "squeezing").

In this squeezing, the degree of this compression or loosening of the filtering member 21 may be optionally selected and has nothing to do with the compressive force for setting the aforementioned first porosity and second porosity.

The frequency of the squeezing may be only once. However, it is more preferable that the pumping is repeated a plurality of times, i.e. to repeat the pumping until the air bubble inside the filtering member 21 is sufficiently removed. Specific example of the frequency of the squeezing where the air bubble inside the filtering member 21 can be sufficiently removed may be the frequency wherein the pumping is repeated until the ascending of air bubble inside the third tube 50 is no more recognized.

As other examples of the de-gassing manipulation, a method to apply a vibration or an acceleration to the filter device 2, or a method of rapidly passing a priming liquid through the filter device 2 may be employed.

This de-gassing manipulation can be performed at any time if it is performed after a priming liquid has been introduced into the filter device 2 but before a liquid to be treated is allowed to pass through the filter device 2.

[2] Then, while the filtering member 21 is left loosened, the first, second, third and fourth clamps are set to the opened and closed patterns as shown in Table 1.

As a result, a portion of the priming liquid stored in the storage container 52 is introduced into the second tube 40 via the third tube 50 and the first connector 7, thereby causing the air inside the second tube 40 to be substituted by the priming liquid.

By the elimination of the air inside the second tube 40 in this manner, it becomes possible to prevent the air inside the second tube 40 from moving into the filter device 2 on the occasion of feeding a liquid to be treated from the storage container thereof to the filter device 2, whereby the effective membrane area of the filtering member 21 can be prevented from being substantially reduced.

[3] Then, the first, second, third and fourth clamps are set to the opened and closed patterns as shown in Table 1, and the porosity of the filtering member 21 is set to the first porosity which is suited for capturing an objective cell (the filtering member 21 is compressed).

When the filtering member 21 is compressed, the volumetric capacity of the filter device 2 is reduced, resulting in the discharging of a portion of priming liquid existing inside the filter device from the first port 2211, the volume of which corresponding to the reduction of the volumetric capacity of the filter device 2. If the third clamp 51 is left opened in advance in this case, an escape passageway of the liquid can be ensured, thus enabling the filtering member 21 to be compressed without an increase in inner pressure of the filter device 2.

An excessive quantity of priming liquid overflowed from the first port 2211 of the filter device 2 can be introduced via the third tube 50 into the storage container 52 and stored therein.

[4] Then, while the filtering member 21 is kept compressed, the first, second, third and fourth clamps are set to the opened and closed patterns as shown in Table 1.

As a result, a liquid to be treated can be fed from the storage container thereof to the filter device 2 via the second bottle-puncturing needle 42, the second tube 40 and the first connector 7.

The objective cell can be captured and isolated by the filtering member 21 when the liquid to be processed passes through the filter device 2. The liquid passed through the filter device 2 is then introduced via the second connector 8 and the fourth tube 60 into the waste liquid container 62 and stored therein.

On this occasion, the liquid to be treated passes through the filter device 2 from the upper side to the lower side thereof as viewed in FIG. 1. In other words, the direction in which the priming liquid passes through the filter member 21 in the step of priming [1] is opposite from the passing direction of the liquid to be treated. As a result, the washing of the inner wall of the storage container of the liquid to be treated in the next step can be facilitated.

Since an objective cell can be captured and isolated by simply permitting the liquid to be treated to pass through the filtering device 2 according to this invention, the operations involved therein are very simple, thus making it possible to easily isolate and recover the objective cell.

[5] Then, while the filtering member 21 is kept compressed, the first, second, third and fourth clamps are set to the opened and closed patterns as shown in Table 1.

As a result, a part of the priming liquid stored in the storage container 52 can be introduced as a washing liquid into the storage container of the liquid to be treated via the third tube 50, the first connector 7, the second tube 40 and the second bottle-puncturing needle 42.

In this case, the storage container of the liquid to be treated is shaken for example so as to wash the inner wall of this storage container by means of the washing liquid that has been introduced into this storage container.

By washing the interior of the storage container of the liquid to be treated in this manner, the objective cell remained in the storage container of the liquid to be treated can be fed to the filter device 2, thus enhancing the recovery ratio of objective cell.

[6] Then, while the filtering member 21 is kept compressed, the first, second, third and fourth clamps are set to the opened and closed patterns as shown in Table 1.

As a result, the washing liquid which has been introduced into the storage container of the liquid to be treated and contains the residual objective cell is fed to the filter device 2 via the second bottle-puncturing needle 42, the second tube 40 and the first connector 7.

As the washing liquid employed for washing the interior of the storage container of the liquid to be treated is fed to the filter device 2, the objective cell that has been left remained in this storage container is also captured by the filtering member 21 during the washing liquid is allowed to pass through the filter device 2.

The washing liquid passed through the filter device 2 is then introduced via the second connector 8 and the fourth tube 60 into the waste liquid container 62 and stored therein.

At that time, the washing liquid is passed through the filter device 2 from the upper side to the lower side thereof. As a result of the operations in aforementioned step [5] and this step, the inner wall of the second tube 40 is washed. As a result, unwanted materials are more effectively inhibited from entering into the recovery liquid on the occasion of recovering an objective cell.

[7] Then, while the filtering member 21 is kept compressed, the first, second, third and fourth clamps are set to the opened and closed patterns as shown in Table 1.

As a result, the priming liquid that has been stored in the storage container 52 is fed as a washing liquid to the filter device 2 via the third tube 50 and the first connector 7.

The washing liquid fed to the filter device 2 is then introduced into the waste liquid container 62 through the filter device 2, the second connector 8 and the fourth tube 60, and then stored in the waste liquid container 62.

When the washing liquid passes through the filter device 2, unwanted materials other than the objective cell that have been adhered onto the filtering member 21 can be washed out and discharged, thus making it possible to prevent the unwanted materials from entering into the recovery liquid on the occasion of recovering the objective cell.

The washing liquid is caused to pass through the filter device 2 from the upper side to the lower side thereof. In other words, the direction in which the priming liquid passes through the filter member 21 in the step of priming [1] is opposite from the passing direction of the washing liquid in this step, whereas the direction in which the liquid to be treated passes through the filter member 21 in the step of filtering [4] is the same as the passing direction of the washing liquid in this step.

Since the direction in which the liquid to be treated passes through the filter member 21 is the same as the passing direction of the washing liquid in this step, the waste liquid container of the treated liquid can be employed also as the waste liquid container of the washing liquid. Namely, according to the cell-isolating and recovering apparatus 1, the waste liquid that has passed through the filter device 2 can be all stored in the waste container 62.

Since the direction in which the priming liquid passes through the filter member 21 is opposite from the passing direction of the washing liquid, the washing efficiency can be enhanced. Additionally, it is easy to employ the priming liquid as a washing liquid.

Since a liquid stored in the storage container 52, i.e. an excessive amount of the priming liquid that has passed through the filtering member 21 is employed as a washing liquid, it is no more required to separately prepare a fresh washing liquid for washing the filter device 2.

Therefore, it is now possible to save the washing liquid for washing the filter device 2. In particular, in case that the priming liquid is designed to contain a rare component or an expensive reagent and the washing liquid is required to employ the same kind of component or reagent as in the priming liquid, it is now possible to save such a rare component or expensive reagent by employing the priming liquid again as the washing liquid.

Therefore, according to this invention, it is possible to reduce the cost for isolating and recovering an objective cell.

[8] Then, the first, second, third and fourth clamps are set to the opened and closed patterns as shown in Table 1, and the filtering member 21 is set to the second porosity which is suited for the release of objective cell (the filtering member 21 is loosened).

By loosening the filtering member 21 in this manner, the captured objective cell can be released into the recovery liquid which is passed through the filter device 2.

As the filtering member 21 is loosened, the volumetric capacity of the filter device 2 is increased. When the first clamp 31 is opened in advance in this case, the recovery liquid can be supplied from the first line 3, so that the filtering member 21 can be loosened without obstruction due to the decrease of inner pressure in the filter device 2.

If the composition of the recovery liquid is desired to be changed from the composition of the priming liquid, the first tube 30 should be sterilely reconnected with another container containing the recovery liquid from its previous connection with the priming liquid storage container by making use of an sterile tube-connecting device before the filtering member 21 is loosened.

This procedure should preferably be performed with all clamps including the first clamp 31 to the fourth clamp 61 being closed so as to avoid the unnecessary movement of liquid inside the cell-isolating and recovering apparatus 1.

When the composition of the recovery liquid is same as that of the priming liquid, the aforementioned procedures are not required.

[9] Then, while the filtering member 21 is kept loosened, the first, second, third and fourth clamps are set to the opened and closed patterns as shown in Table 1.

As a result, the recovering liquid is fed from the priming liquid storage container to the filter device 2 via the first bottle-puncturing needle 32, the first tube 30 and the second connector 8.

When the recovery liquid fed to the filter device 2 is caused to pass through the filter device 2, the objective cell that has been captured in the filtering member 21 is allowed to be released into the recovery liquid from the filtering member 21.

The recovering liquid which passed through the filtering member 21 is then introduced into and stored in the storage container 52 through the first connector 7 and the third tube 50.

On this occasion, the recovery liquid is passed through the filter device 2 from the lower side to the upper side thereof as viewed in FIG. 1. Namely, the direction in which the washing liquid passes through the filter member 21 in the step of washing [7] is opposite from the passing direction of the recovery liquid in this step.

As a result, the storage container 52 can be easily employed not only as a container for storing the washing liquid but also as a container for recovering the objective cell. Moreover, if each high molecular porous membrane 211 of the filtering member 21 is provided with a gradient in physical or chemical property, the objective cell can be effectively recovered using a relatively small quantity of recovering liquid.

Note that it may be preferable to perform a detaching operation which momentarily changes the flowing direction or flowing velocity of the recovery liquid at or near the filtering member 21 during the recovery of the objective cell. If such a detaching operation is performed, the release of objective cell from the filtering member 21 can be promoted, thus enhancing the recovering ratio of objective cell.

This detaching operation may be performed by means of conducting the pumping once or a plurality of times. As other examples of the detaching operation, a method of applying vibration or acceleration to the filter device 2 may be adopted.

[10] After the objective cell is released from the filtering member 21 and the recovery liquid containing the objective cell is collected into the storage container 52, the third tube 50 is sealed using a tube sealer for instance, and then, this sealed portion is cut off.

According to the aforementioned procedures, the objective cell can be aseptically recovered into the storage container 52.

It should be noted that any one or more procedures among the aforementioned steps [2], [5], [6], [10] may be omitted.

Further, instead of performing the step [2], the step [3] may be performed as follows. Specifically, the first clamp 31, the third clamp 51 and the fourth clamp 61 are closed, and the second clamp 41 is opened, and at the same time, the filtering member 21 is compressed, thereby allowing an excessive quantity of priming liquid in the filter device 2 to be introduced into the second tube 40, thus substituting the priming liquid for the air inside the second tube 40.

If the step [3] is performed in the manner described above, the step [2] can be omitted while enabling the compression of the filtering member 21 and the priming of the interior of second tube 40 to be performed in a single step, thus simplifying the manipulation of these steps.

According to one embodiment of the aforementioned processing method, the priming liquid, the liquid to be treated, the washing liquid and the recovery liquid were all caused to naturally flow under the gravitation. However, the positional relationship of the priming liquid storage container, the storage container 52, the storage container of the liquid to be treated, the filter device 2 and the storage container 62 may be altered from the aforementioned embodiment.

Further, according to one embodiment of the aforementioned processing method, the priming liquid, the liquid to be treated, the washing liquid and the recovery liquid were all caused to naturally flow under the gravitation thereof. However, other methods using a low flow rate pump such as a roller pump for transferring the aforementioned liquids may be employed.

Although this invention has been explained with reference to the aforementioned preferable embodiment shown in the drawings, this invention is not restricted to such embodiment.

For example, the opening and closing means for selectively opening and closing the passage of liquid flow through the first tube 30, the second tube 40, the third tube 50 and the fourth tube 60 may be a Kocher clamp, a cock or a valve other than the aforementioned clamp.

Further, the other end of the first tube 30 and of the second tube 40 may not be connected with a bottle-puncturing needle, but may be connected with a connector, a three-way stopcock, a blood bag, a syringe needle, an air filter, etc. Additionally, they may be connected with these tubes through a fusion bonding.

The first connector 7 may be an ⊦-shaped tube instead of the Y-shaped tube. Likewise, the second connector 8 may be a Y-shaped tube instead of the ⊦-shaped tube.

In addition, As for the first connector 7, the branch tube connected with the second tube 40 and the branch tube connected with the third tube 50, i.e. the first branch tube 71 and the second branch tube 72 may be connected with each other not at an acute angle. For example, the first connector 7 may be constituted by a T-shaped tube.

Likewise, as for the second connector 8, the branch tube connected with the first tube 30 and the branch tube connected with the line communicated with the filter device 2, i.e. the first branch tube 81 and the second branch tube 82 may be connected with each other not at an acute angle. For example, the second connector 8 may be constituted by a T-shaped tube.

EXAMPLE 1

[1] A filter device having a construction as shown in FIG. 2 was manufactured.

The volumetric capacity of the housing was set to the range of 20 to 40 mL. As for the filtering member, a laminate consisting of six sheets of polyurethane porous sheet having a larger pore size on the first port 2211 side and one sheet of polyurethane porous sheet having a smaller pore size on the second port 2221 side was employed. Each polyurethane porous sheet employed herein was 60 mm in effective diameter and 0.6 mm in thickness. The total thickness of the laminate was 4.2 mm.

Further, a polypropylene mesh was interposed between one surface of the laminated filtering member and an upstream spacer 23a, and between the other surface of the laminated filtering member and a downstream spacer 23b.

By using the porosity-setting means, the average pore size and porosity of the filtering member were measured under the condition where a compressive force is not applied to the filtering member, and under the condition where a compressive force is applied to the filtering member so as to compress the filtering member to a total thickness of 1.9 mm.

As a result, under the non-compressed state, the average pore size of the porous sheet having a larger pore size was 15 $\mu$m, and the porosity thereof was 83%, while the average pore size of the porous sheet having a smaller pore size was 7 $\mu$m, and the porosity thereof was 83%. On the other hand, under the compressed state, the average pore size of the porous sheet having a larger pore size was 3 μm, and the porosity thereof was 61%, while the average pore size of the porous sheet having a smaller pore size was 2 μm, and the porosity thereof was 61%.

By the way, the measurement of the average pore size of the porous sheet was performed using a palmporometer (PMI Automated Capillary Flow Porometer, PMI (Porocymaterial Co., Ltd.)), and the measurement of the porosity of the porous sheet was performed based on the true specific gravity and bulk density of the polyurethane.

[2] By making use of this filter device and the cell-isolating and recovering apparatus shown in FIG. 1, experiments to isolate and recover lymphocyte (objective cell) from human whole blood (liquid to be treated) were performed.

Incidentally, the volumetric capacity of the storage container 52 was 200 mL, while the volumetric capacity of the waste liquid container 62 was 350 mL.

First of all, the first bottle-puncturing needle 32 was pierced into the rubber plug of a bag (priming liquid storage container) filled with a 0.5% albumin-containing physiological saline, thereby connecting the first tube 30 with the bag filled with a 0.5% albumin-containing physiological saline. This 0.5% albumin-containing physiological saline was employed as a priming liquid (a washing liquid) and as a recovery liquid in the following procedures.

Further, the second bottle-puncturing needle 42 was pierced into the connecting port of a bag (storage container of a liquid to be treated) filled with human whole blood containing an anticoagulant (citric acid), thereby connecting the second tube 40 with the bag filled with the human whole blood. Specifically, this bag was filled with 100 mL of the human whole blood.

As a result, the cell-isolating and recovering apparatus was constructed into a closed system.

Next, the cell-isolating and recovering apparatus constituting a closed system was arranged such that the filter device 2 was disposed higher than the waste liquid container 62, that storage container of the liquid to be treated was disposed higher than the filter device 2, that the storage container 52 was disposed higher than the storage container to be treated, and that the priming liquid storage container was disposed higher than the storage container 52. Namely, the cell-isolating and recovering apparatus 1 was set such that the priming liquid storage container, the storage container 52, the storage container to be treated, the filter device 2 and the waste liquid container 62 were arranged at the levels which became lower in the mentioned order.

As a result of this arrangement, the supply of the liquids required in the following procedures was effected due to the differences of the height among these containers, i.e. under the natural flow-down due to the gravitation of each liquid.

[2.1] Next, the second clamp 41 and the fourth clamp 61 were closed, while the first clamp 31 and the third clamp 51 were opened.

As a result, the priming liquid was fed from the priming storage container to the filter device 2 via the first bottle-puncturing needle 32, the first tube 30 and the second connector 8, thereby enabling the filtering member 21 of the filter device 2 to be impregnated with the priming liquid.

An excessive quantity of the priming liquid that had passed through the filter device 2 was allowed to pass through the first connector 7 and the third tube 50 into the storage container 52 and stored therein.

It was recognized in this case that the air existed in the filter device 2 was smoothly moved toward and passed through the third tube 50. Therefore, it was confirmed that the air inside the filter device 2 was smoothly replaced by the priming liquid.

This operation was performed with the filtering member 21 being released from the compression force.

The volume of the priming liquid that was supplied to the filter device 2 was 110 mL in total, which was supplied to the filter device 2 taking about one minute.

[2.2] Next, the first clamp 31 and the fourth clamp 61 were closed, while the second clamp 41 and the third clamp 51 were opened.

As a result, a part of the priming liquid that had been stored in the storage container 52 was introduced into the second tube 40 via the third tube 50 and the first connector 7, thereby eliminating the air inside the second tube 40.

[2.3] Next, the third clamp 51, the second clamp 41 and the fourth clamp 61 were all closed, while the first clamp 31 was opened, and then, the filtering member 21 was compressed using a porosity-setting means.

[2.4] Next, the first clamp 31 and the third clamp 51 were closed, while the second clamp 41 and the fourth clamp 61 were opened.

As a result, all of the liquid to be treated was introduced from the storage container thereof into the filter device 2 via the second bottle-puncturing needle 42, the second tube 40 and the first connector 7, and then, the liquid was transferred to and stored in the waste liquid container 62 after passing through the filter device 2, the second connector 8 and the fourth tube 60.

The time required for all of the liquid to be treated to pass through the filter device 2 (hereinafter referred to as filtration time) was about 6 minutes.

[2.5] Next, the first clamp 31 and the fourth clamp 61 were closed, while the second clamp 41 and the third clamp 51 were opened.

As a result, a part of the priming liquid that had been stored in the storage container 52 was allowed to pass through the third tube 50 and the first connector 7, the second tub 40 and the second bottle-puncturing needle 42, and then, introduced into the storage container for the liquid to be treated.

On this occasion, the storage container for the liquid to be treated was shaken to wash the inner wall of the container with the washing liquid introduced therein.

[2.6] Next, the first clamp 31 and the third clamp 51 were closed, while the second clamp 41 and the fourth clamp 61 were opened.

As a result, the washing liquid that had been stored in the storage container for the liquid to be treated was allowed to pass through the second bottle-puncturing needle 42, the second tube 40 and the first connector 7, and then, introduced into the filter device 2. The liquid to be treated introduced into the filter device 2 was then allowed to pass through the second connector 8 and the fourth tube 60, and then, stored in the waste liquid container 62.

As a result of the above step [2.5] and this operation, the liquid to be treated which slightly remained on the inner wall of the second tube 40 could be washed out.

[2.7] Next, the first clamp 31 and the second clamp 41 were closed, while the third clamp 51 and the fourth clamp 61 were opened.

As a result, the priming liquid that had been stored in the storage container 52 was allowed to pass through the third tube 50 and the first connector 7, and then, introduced into the filter device 2. The priming liquid introduced into the filter device 2 was then allowed to pass through the second connector 8 and the fourth tube 60, and then, stored in the waste liquid container 62.

The quantity of the washing liquid which was fed from the storage container to the filter device 2 was 70 mL, which was supplied to the filter device 2 taking about two minutes.

It should be noted that, according to the conventional method, even if the above steps [2.5] and [2.6] were omitted, 70 mL of a fresh albumin-containing physiological saline is required as a washing liquid. By contrast, since the priming liquid that was employed for impregnating the filter device 2 could be re-used as a washing liquid according to this example, it was made possible to save 70 mL of an albumin-containing physiological saline.

[2.8] Next, the second clamp 41, the third clamp 51 and the fourth clamp 61 were all closed, while the first clamp 31 was opened, and then, the filtering member 21 was loosened using a porosity-setting means.

[2.9] Next, the second clamp 41 and the fourth clamp 61 were closed, while the first clamp 31 and the third clamp 51 were opened.

As a result, the recovery liquid was introduced from the priming liquid storage container into the filter device 2 via the first bottle-puncturing needle 42, the first tube 30 and the second connector 8, and then, the recovery liquid was further transferred to and stored in the storage container 52 after passing through the filter device 2, the first connector 7 and the third tube 50.

The quantity of the recovery liquid which was fed to the filter device 2 was 100 mL, which was fed to the filter device 2 taking about one minute.

[3] Thereafter, the number of cell in the recovery liquid that had been stored in the storage container 52 was measured using a cell-counting apparatus, thus determining the recovery ratio of the lymphocyte. Likewise, the recovery ratios of erythrocyte and platelet which were unwanted components in the recovery liquid were also determined.

EXAMPLE 2

Experiments were conducted in the same manner as in Example 1 except that the squeezing was performed as a de-gassing operation during the step of priming (the aforementioned step [2.1]).

The squeezing was repeated until the float-up of air bubble inside the third tube 50 was no more recognized.

EXAMPLE 3

Experiments were conducted in the same manner as in Example 1 except that the squeezing was performed as a detaching operation during the step of recovering the objective cell (the aforementioned step [2.9]).

The squeezing was performed repeating the compression and releasing of the filtering member 21 five to six times during the recovering step of the objective cell.

EXAMPLE 4

Experiments were conducted in the same manner as in Example 1 except that the squeezing was performed as a de-gassing operation during the step of priming (the aforementioned step [2.1]) and that the squeezing was additionally performed as a detaching operation during the step of recovering the objective cell (the aforementioned step [2.9]).

The squeezing on the occasion of the priming step was repeated until the float-up of air bubble inside the third tube 50 was no more recognized, whereas the pumping on the occasion of the recovering step was performed repeating the compression and releasing of the filtering member 21 five to six times during the recovering of the objective cell.

EXAMPLE 5

An experiment was conducted in the same manner as in Example 4 except that a T-shaped tube was substituted for the Y-shaped tube which was employed for constituting the first connector 7 of the cell-isolating and recovering apparatus, and that a T-shaped tube was substituted for the ⊦-shaped tube which was employed for constituting the second connector 8.

Namely, in this Example, the first branch tube 71 and the second branch tube 72 of the first connector 7 were branched extending in the opposite direction from each other and forming a straight line, while the first branch tube 81 and the second branch tube 82 of the second connector 8 were branched also extending in the opposite direction from each other and forming a straight line.

Comparative Example 1

Experiments were conducted in the same manner as in Example 1 except that the squeezing (the above step [2.1]) was not performed at all.

Incidentally, the washing liquid employed was supplied by reconnecting the third tube 50 with a container having the same structure as that of the storage container 52 and storing therein 70 mL of 0.5% albumin-containing physiological saline by using an sterile tube-connecting device, after its previous connection with the empty storage container 52 was switched off.

Comparative Example 2

Experiments were conducted in the same manner as in Example 1 except that the washing (the above steps [2.5] to [2.7]) was not performed at all.

Note that, the priming liquid stored in the storage container 52 was eliminated by reconnecting the third tube 50 with an empty container having the same structure as that of the container 52 by using a sterile tube-connecting device, after its previous connection with the storage container 52 containing the washing liquid was switched off.

Comparative Example 3

Experiments were conducted in the same manner as in Example 1 except that the recovery of the objective cell was performed with the filtering member 21 being left in a compressed state, i.e. without loosening the filtering member 21 (hence, the above step [2.8]) was not performed at all).

Comparative Example 4

Experiments were conducted in the same manner as in Example 1 except that the filtration of the liquid to be treated was performed with the filtering member 21 being left in a loosened state, i.e. without compressing the filtering member 21 (hence, the above step [2.3]) was not performed at all).

The conditions of the procedures in the above Examples 1 to 5 and Comparative Examples 1 to 4 are shown in the following Table 2.

TABLE 2

| | Squeezing during priming | Squeezing during recovering | Kinds of connector | Priming | Washing | Filter loosened during recovery | Filter compressed during filtration |
|---|---|---|---|---|---|---|---|
| Example 1 | No | No | Y-shaped tube. | Yes | Yes | Yes | Yes |
| Example 2 | Yes | No | ⊢-shaped Y-shaped tube. | Yes | Yes | Yes | Yes |
| Example 3 | No | Yes | ⊢-shaped Y-shaped tube. | Yes | Yes | Yes | Yes |
| Example 4 | Yes | Yes | ⊢-shaped Y-shaped tube. | Yes | Yes | Yes | Yes |
| Example 5 | Yes | Yes | ⊢-shaped T-shaped tube | Yes | Yes | Yes | Yes |
| Comparative Example 1 | No | No | Y-shaped tube. | No | Yes | Yes | Yes |
| Comparative Example 2 | No | No | ⊢-shaped Y-shaped tube. | Yes | No | Yes | Yes |
| Comparative Example 3 | No | No | ⊢-shaped Y-shaped tube. | Yes | Yes | No | Yes |
| Comparative Example 4 | No | No | ⊢-shaped Y-shaped tube. ⊢-shaped | Yes | Yes | Yes | No |

The filtration time and the recovery ratios of lymphocyte, erythrocyte and platelet in the above Examples 1 to 5 and Comparative Examples 1 to 4 are shown in the following Table 3.

TABLE 3

| | Filtration time (min.) | Recovery ratio of lymphocyte (%) | Recovery ratio of erythrocyte (%) | Recovery ratio of platelet (%) |
|---|---|---|---|---|
| Example 1 | 6.5 | 78 | 1.0 | 6.6 |
| Example 2 | 6.0 | 77 | 1.1 | 7.0 |
| Example 3 | 6.6 | 91 | 1.6 | 7.8 |
| Example 4 | 5.9 | 92 | 0.7 | 7.6 |
| Example 5 | 5.9 | 92 | 2.3 | 9.3 |
| Comparative Example 1 | 8.8 | 72 | 1.6 | 6.4 |
| Comparative Example 2 | 6.7 | 80 | 5.1 | 17.3 |
| Comparative Example 3 | 6.4 | 35 | 1.1 | 6.5 |
| Comparative Example 4 | 2.5 | 25 | 1.6 | 8.0 |

As seen from the results of Table 3, it was confirmed from Example 1 that lymphocyte was isolated and recovered from human whole blood at a very high recovery ratio. It was also confirmed that the unwanted components such as erythrocyte and platelet were very effectively eliminated, i.e. lymphocyte of very high purity was recovered. It was also confirmed that the isolation and the recovery of objective cell ware effectively performed within a short period of filtration.

As seen from the results of Table 3, it was confirmed from Example 2 that lymphocyte was isolated and recovered from human whole blood at a very high recovery ratio as in the case of Example 1. It was also confirmed that, as in the case of Example 1, the unwanted components such as erythrocyte and platelet were very effectively eliminated, i.e. lymphocyte of very high purity was recovered.

Moreover, it was possible to shorten the filtration time as compared with that of Example 1. Therefore, it was confirmed that when the de-gassing manipulation was performed prior to the feeding of the liquid to be treated into the filter device 2, the filtration time was shortened further, and at the same time, the isolation and the recovery of objective cell were more effectively performed.

As seen from the results of Table 3, it was confirmed from Example 3 that lymphocyte was isolated and recovered from human whole blood at a higher recovery ratio as compared with Example 1. It was also confirmed that the unwanted components such as erythrocyte and platelet were very effectively eliminated as in the case of Example 1, i.e. lymphocyte of very high purity was recovered. It was also confirmed from the results of Table 3 that the recovery ratio of objective cell was further enhanced by conducting the detaching operation during the recovery of objective cell.

It was also confirmed that the isolation and the recovery of objective cell were effectively performed within a short period of filtration as in the case of Example 1.

As seen from the results of Table 3, it was confirmed from Example 4 that lymphocyte was isolated and recovered from human whole blood at a higher recovery ratio as compared with Example 1. It was also confirmed that the unwanted components such as erythrocyte and platelet were very effectively eliminated as in the case of Example 1, i.e. lymphocyte of very high purity was recovered. It was also confirmed from the results of Table 3 that the recovery ratio of objective cell was further enhanced by conducting the detaching operation during the recovery of objective cell.

Moreover, it was possible to shorten the filtration time as compared with that of Example 1. Therefore, it was confirmed that when the de-gassing manipulation was performed prior to the feeding of the liquid to be treated into the filter device 2, the filtration time was shortened further, and at the same time, the isolation and the recovery of objective cell were more effectively performed.

As seen from the results of Table 3, it was confirmed from Example 5 that lymphocyte was isolated and recovered from human whole blood at a very high recovery ratio as in the case of Example 4. It was also confirmed that, similar to Example 4, the unwanted components such as erythrocyte and platelet were very effectively eliminated, i.e. lymphocyte of very high purity could be recovered.

It was also confirmed that the isolation and recovery of objective cell could be effectively performed within a short period of filtration as in the case of Example 4.

It was also confirmed that the survival ratio and function of the lymphocyte after the recovery thereof in Examples 1 to 5 were the same as those of the lymphocyte in the human whole blood which had been stored in the storage container before these experiments, and no damage was recognized in the lymphocyte after the recovery thereof.

As seen from the results of Table 3, it was confirmed from Comparative Example 1 where no priming was conducted that it takes a very long period of time for the filtration, thus failing to effectively perform the isolation and recovery of objective cell. The reason thereof may be ascribed to the fact that a large quantity of air bubble is existed in the filter device 2 as well as in the filtering member 21, thereby substantially reducing the effective surface area of the filtering member 21.

As seen from the results of Table 3, it was confirmed from Comparative Example 2 where the washing was not conducted that the unwanted components such as erythrocyte and platelet were allowed to enter into the recovery liquid, thus merely making it possible to recover lymphocyte of low purity. The reason thereof may be ascribed to the fact that the unwanted materials left remained in the filter device 21 or adhered onto the filtering member 21 were allowed to enter into the recovery liquid upon recovering the objective cell.

As seen from the results of Table 3, it was confirmed from Comparative Example 3 where the recovery of objective cell was conducted without loosening the filtering member 21 that the lymphocyte was hardly recovered. The reason thereof may be ascribed to the fact that the objective cell was hardly detached from the filtering member 21 at the time when the recovery liquid passed through the filtering member 21, thus failing to release the lymphocyte into the recovery liquid.

As seen from the results of Table 3, it was confirmed from Comparative Example 4 where the filtration of liquid to be treated was conducted without compressing the filtering member 21 that the lymphocyte was hardly recovered. The reason thereof may be ascribed to the fact that the objective cell was hardly captured by the filtering member 21 at the time when the liquid to be treated passed through the filtering member 21.

As explained above in detail, according to this invention, it is possible according to isolate and recover an objective cell in a closed system, thus making it possible to sterilely perform the isolation and recovery of objective cell.

Moreover, since the cell-isolating and recovering apparatus is simple in construction, the process and cost for manufacturing such an apparatus can be also saved.

Moreover, since the filtration can be performed within a short period of time and at the same time, since the isolation and recovery of objective cell can be performed at a high recovery ratio, the isolation and recovery of objective cell can be performed effectively.

Additionally, since the quantity of the liquid employed for the priming and washing can be minimized, the isolation and recovery of objective cell can be performed at low cost. In particular, where a rare component or an expensive reagent is required as an ingredient of such a liquid, the cost involved in the method can be extremely reduced, thus making the method very useful.

Furthermore, if the de-gassing operation is performed during the time period between the initiation of the priming and the isolation of objective cell, the filtration time can be shortened, the recovery ratio can be enhanced, and the efficiency of the isolation and recovery of objective cell can be further enhanced. Furthermore, if the detaching operation is performed on the occasion of recovering objective cell, the recovery ratio of objective cell can be further enhanced.

Additionally, if the connector to be connected with the line for feeding a liquid to be treated into the filter device and with the line provided with a storage container for storing a priming liquid that has passed through the filter device is formed of an ⊦-shaped or Y-shaped tube, lymphocyte of high purity can be isolated and recovered at a high yield.

Moreover, if the connector to be connected with the line for feeding a priming liquid to the filter device and with the line communicating with the filter device is formed of an ⊦-shaped or Y-shaped tube, lymphocyte of higher purity can be isolated and recovered at a higher yield.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of isolating and recovering an objective cell by using a device comprising a filtering member which is formed of a porous body and capable of changing the porosity thereof, a first line for feeding a priming liquid to said filtering member, and a second line for feeding a liquid to be treated containing the objective cell to said filtering member, a third line provided with a storage container for storing the priming liquid that has been passed through the filtering member, a fourth line for discharging a waste liquid such as the liquid to be treated that has passed through the filtering member, a first connector for connecting the second line and the third line to communicate the second and third lines with the filtering member, and a second connector for connecting the first line and fourth line to communicate the first and fourth lines with the filtering member; said method comprising;

performing a priming by feeding said priming liquid through said first line thereby impregnating said filtering member with said priming liquid, while allowing an excessive quantity of said priming liquid that has passed through said filtering member to be stored in the storage container;

isolating said objective cell by feeding said liquid to be treated through said second line so as to pass said liquid to be treated through said filtering member under a condition where the porosity of said filtering ember is set to a first porosity which enables said objective cell to be captured, thereby performing the isolation of said objective cell;

washing said filtering member by causing said priming liquid stored in said storage container during said priming step to pass through said filtering member again; and recovering said objective cell captured in said filtering member by causing a recovery liquid to pass through said filtering member under a condition where the porosity of said filtering member is set to a second porosity which is larger than said first porosity.

2. The method according to claim 1, wherein said washing step includes also a washing of said second line.

3. The method according to claim 1, wherein a sequence of said steps are performed in a closed system.

4. The method according to claim 1, wherein said recovering liquid is fed through said first line.

5. The method according to claim 1, wherein said objective cell is recovered in said storage container.

* * * * *